(12) United States Patent
Thompson et al.

(10) Patent No.: US 10,143,204 B2
(45) Date of Patent: *Dec. 4, 2018

(54) CONCENTRATED SABADILLA EXTRACT

(71) Applicant: McLaughlin Gormley King Company, Golden Valley, MN (US)

(72) Inventors: Dain Andrews Thompson, Golden Valley, MN (US); John Thomas Bergman, Saint Louis Park, MN (US); Darrick David Unger, Minnetonka, MN (US)

(73) Assignee: MCLAUGHLIN GORMLEY KING COMPANY, Golden Valley, MN (US)

( * ) Notice: Subject to any disclaimer, the term of this patent is extended or adjusted under 35 U.S.C. 154(b) by 287 days.

This patent is subject to a terminal disclaimer.

(21) Appl. No.: 15/299,843

(22) Filed: Oct. 21, 2016

(65) Prior Publication Data

US 2017/0112141 A1 Apr. 27, 2017

Related U.S. Application Data

(60) Provisional application No. 62/244,908, filed on Oct. 22, 2015.

(51) Int. Cl.
*A61K 36/00* (2006.01)
*A01N 65/40* (2009.01)
*A01N 65/42* (2009.01)

(52) U.S. Cl.
CPC ............. *A01N 65/40* (2013.01); *A01N 65/42* (2013.01); *Y02A 50/324* (2018.01)

(58) Field of Classification Search
CPC ...................................................... A61K 36/00
USPC ............................................................ 424/725
See application file for complete search history.

(56) References Cited

U.S. PATENT DOCUMENTS

| | | | |
|---|---|---|---|
| 2,348,949 A * | 5/1944 | Allen | A01N 65/00 424/753 |
| 2,390,911 A | 12/1945 | Allen et al. | |
| 3,078,211 A | 2/1963 | Allison et al. | |
| 6,309,678 B1 | 10/2001 | Kahol et al. | |
| 2015/0216181 A1 | 8/2015 | Hernandez et al. | |
| 2015/0223456 A1 | 8/2015 | Pitterna et al. | |

OTHER PUBLICATIONS

International Search Report and Written Opinion issued by the International Bureau in corresponding application No. PCT/US2016/058070 dated Jan. 17, 2017.

* cited by examiner

*Primary Examiner* — Michael V Meller
(74) *Attorney, Agent, or Firm* — Wood, Phillips, Katz, Clark & Mortimer

(57) ABSTRACT

The invention relates to methods for preparing a concentrated sabadilla extract and to methods of its use as a pesticide.

1 Claim, No Drawings

US 10,143,204 B2

CONCENTRATED SABADILLA EXTRACT

FIELD OF THE INVENTION

The present invention is directed to methods of preparing a concentrated sabadilla extract and methods of its use as a pesticide.

BACKGROUND OF THE INVENTION

Controlling damaging pests on plants grown to provide human food is a constant struggle for growers. Insects can completely destroy a harvest and can cause catastrophic food shortages or financial ruin for the growers. Although many products are effective against insects that damage plants, the products must also be safe enough to be released into the growing environment and safe enough to be applied to parts of the plants that will eventually be consumed.

Organic farming is increasing in popularity. Organic farming restricts the use of compounds that are used for pest control to encourage sustainability and safety. Pesticides can be used in organic farming if they are considered "natural." Unfortunately, many of the natural insecticides currently available are not potent enough to provide adequate insect control. Further, many of the currently available natural pesticides are not practical to apply or their application is cost prohibitive.

One effective naturally derived insecticide is found in the tissues of many of the plants of the genus *Schoenocaulon*, commonly referred to as sabadilla. The species with the longest history of use, and the most readily available, is *Schoenocaulon officinale*. The plant is indigenous to Central and South America and its seeds have been used for centuries for their insecticidal properties. The seeds contain the alkaloids veratridine and cevadine, both of which are known to be active against arthropods.

Usually the dried seeds are ground to a powder and the powder is applied dry or wetted to the insects or their environment. The seeds must be milled into smaller particles in order to be applied to the insects. The milling process usually requires an oil absorbing adjuvant to prevent the seeds from caking. This adjuvant dilutes the alkaloids in the ground seeds. Also, the ground seeds can be difficult to apply to areas in need of treatment because the seeds' particles and anti-caking adjuvant can clog spraying equipment. Another disadvantage of using ground seeds is that the dust from the seeds can cause eye and nasal irritation. Further, the ground seed powder is often not potent enough to control large infestations.

U.S. Pat. Nos. 2,348,949 and 2,390,911 disclose the use of ground sabadilla seeds with beta-butoxy-beta-prime-thiocyanodiethyl-ether to control houseflies. Further, these patents teach heating the seeds and using them as a powder, or mixing them with kerosene to form a sprayable formulation. Neither of these disclosed mixtures of ground sabadilla seeds would be appropriate for organic farming.

Accordingly, there is a need for new methods of controlling insects. The methods should be potent, safe for growers to apply, safe to beneficial organisms (target specific), and safe for the environment.

SUMMARY OF THE INVENTION

In one aspect, the present invention is directed to methods for preparing sabadilla extract.

In another aspect, the present invention is directed to methods for controlling pests comprising applying sabadilla extract to pests or to their environment.

In a further aspect, the present invention is directed to a concentrated pesticidal sabadilla extract product produced by the process comprising the steps of milling sabadilla seeds or other plant parts, washing the milled sabadilla seeds or other plant parts with at least one seed and plant part solvent selected from the group consisting of methanol, ethanol, glycol ether, ethyl lactate, propanol, butyl lactate, gamma-butyrolactone, and 1-butanol under agitation to produce a solution of sabadilla extract in the seed and plant part solvent, removing the solution from the washed milled seeds, and removing the seed and plant part solvent from the solution to produce the sabadilla extract.

In a preferred embodiment, the sabadilla extract is prepared from Sabadilla seeds.

DETAILED DESCRIPTION OF THE INVENTION

Applicant has unexpectedly developed new methods of producing a concentrated sabadilla extract. Applicant was able to develop a method to remove the solid inert seed parts, such as the cellulose, hemicellulose, lignin and pectin, from the rest of the seed components with methanol. This method produces an extract that contains the alkaloids in a more concentrated form. This method generally involves using a solvent to separate the solid inert seed or other plant parts from the resin, oil, and active compounds in the seed or plant. The resin, oil and active compounds are dissolved in the solvent, such as methanol, during agitation with milled seeds or other plant parts. The concentrated sabadilla extract remains when the solvent and washed milled seeds or plant parts are removed.

The concentrated sabadilla extract is more effective than ground whole seeds or plant parts because the inert parts of the seeds or plant parts have been removed. Further, the inert parts of the seeds or plant parts can no longer clog spray equipment. Yet another advantage of the concentrated sabadilla extract is that it is easier to handle and can be formulated in various user-friendly products to meet the needs of growers. Applicant's methods for production of the concentrated sabadilla extract are also high yielding and can be easily scaled up for commercial use.

In one embodiment, the present invention is directed to methods for producing concentrated insecticidal sabadilla extract comprising milling sabadilla seeds or other plant parts, washing the milled sabadilla seeds or other plant parts with at least one seed and plant part solvent selected from the group consisting of methanol, ethanol, glycol ether, ethyl lactate, propanol, butyl lactate, gamma-butyrolactone, and 1-butanol under agitation to produce a solution of sabadilla extract in the seed and plant part solvent, removing the solution from the washed milled seeds or other plant parts, and removing the seed and plant part solvent from the solution to produce the sabadilla extract.

Sabadilla seeds and extract may be derived from any species of *Schoenocaulon*. The genus *Schoenocaulon* includes the following species: *Schoenocaulon calcicola*, *Schoenocaulon caricifolium*, *Schoenocaulon comatum*, *Schoenocaulon conzattii*, *Schoenocaulon dubium* (alt. *Schoenocaulon gracile*), *Schoenocaulon framei*, *Schoenocaulon ghiesbreghtii* (alt. *Schoenocaulon drummondii*, *Schoenocaulon yucatanense*), *Schoenocaulon ignigenum*, *Schoenocaulon intermedium*, *Schoenocaulon jaliscense*, *Schoenocaulon macrocarpum* (alt. *Schoenocaulon lauri-* cola), *Schoenocaulon madidorum*, *Schoenocaulon megarrhizum*, *Schoenocaulon mortonii*, *Schoenocaulon oaxacense*, *Schoenocaulon obtusum*, *Schoenocaulon officinale*, *Schoenocaulon pellucidum*, *Schoenocaulon plumosum*, *Schoenocaulon pringlei*, *Schoenocaulon rzedowskii*, *Schoenocaulon tenorioi*, *Schoenocaulon tenue*, *Schoenocaulon tenuifolium*, *Schoenocaulon texanum*, and *Schoenocaulon tigrense*.

In a preferred embodiment, the sabadilla seeds can be derived from *S. officinale*.

To optimize solvent penetration and subsequent extraction, the seed coat must be ruptured and the distance between penetrable surfaces of the seed reduced as much as possible. The can be achieved by milling the seeds.

Sabadilla seeds are very difficult to cleanly break into fine pieces. The bulk of the seed is hard and oily and requires a lot of energy to pulverize, producing heat due to high friction. Any suitable milling method can be used. Applicant found that cryogenic hammer milling the seeds was ideal for efficient extraction of the sabadilla oil.

Cryogenic grinding, or cryomilling, most commonly uses dry ice, liquid carbon dioxide or liquid nitrogen to cool the feed material in a mill of an otherwise conventional design (e.g. a cryogenic hammermill.) This super-cooling makes the sabadilla seed more uniformly brittle, in turn making it easier to control particle size. Additionally, the oil in the seed is a solid at the temperature of liquid nitrogen, and does not slow processing speed. This increased friability and solidification of the oil allows for very efficient throughput rates during milling.

Flake milling, most commonly using a roller-type mill, was found to create a milled sabadilla seed that was somewhat more efficient to handle during processing than cryogenically hammer milled seed, but allowed a less efficient extraction. In a flake milling procedure, the seeds are heated to increase plasticity and passed between rollers which flatten the seeds into thin, solvent-penetrable flakes that are still largely one piece. Flaking usually produces a minimal amount of fine particles which hinder efficient processing.

Pin milling may also be used but this technique produces particles which are coarse and require more time to process than other milling products. Conventional, ambient, hammer milling and "Fitz" milling may also be used to produce a sufficiently sized particle, however, throughput rates are generally inefficient and it is difficult to control particle size.

While flake milling's larger particle size overall makes it simplest and easiest to handle during processing, Applicant found that cryogenic hammer milling allowed the creation of sabadilla seed particles over a range of sizes that enable a more efficient extraction of sabadilla oil with only a modest increase in material handling difficulty. Accordingly, Applicant found that cryogenic hammer milling with liquid nitrogen was a superior milling approach for producing sabadilla oil.

The milled sabadilla seeds can be washed with the seed and plant part solvent one time or multiple times. For example, the milled sabadilla seeds can be washed one to ten times. If the seed and plant part solvent is decanted and additional solvent added (additional washes), then the yield is increased.

In an embodiment, the milled sabadilla seeds are washed the seed and plant part solvent from 1 to 5 times. In a preferred embodiment, the milled sabadilla seeds are washed with the seed and plant part solvent from 2 to 5 times. In a most preferred embodiment, the milled sabadilla seeds are washed with the seed and plant part solvent 5 times.

The sabadilla extract can be washed with the extract solvent one time or multiple times. For example, the sabadilla extract can be washed one to ten times.

In an embodiment, the seed or plant part solvent solution is removed from the washed milled seeds by decanting (pouring), pumping, or draining. For example, when the extract is produced on a small scale, the milled seeds settle to the bottom of the flask and the seed or plant part solvent solution can be easily decanted out of the flask. During commercial extraction production, the seed or plant part solvent solution can be removed by methods known by those of skill in the art. For example, the seed and plant part solution could be removed from the washing vessel by draining the methanol with the use of a screen, pump, or filter.

In another embodiment, sabadilla oil can be extracted from milled sabadilla seeds using countercurrent extraction. Countercurrent extraction is a commercial scale extraction process typically used in oil seed extraction of seeds such as canola and soy. In brief, countercurrent extraction is a continuous process in which fresh, milled seed is fed through a long solvent bath by conveyor. The seed enters one end and the solvent enters the other, both eventually exiting opposite ends of the apparatus as spent marc (i.e. extracted/depleted seed) and miscella (i.e. solvent with a solute load from the seed).

During the extraction, the milled sabadilla seeds and seed or plant part solvent should be agitated. This can be done by any method known by those of skill in the art. Applicant found that stirring the milled sabadilla seeds in the solvent increased the rate of extraction and was an effective means of agitation. The process was most efficient if the stirring was brisk enough to prevent the milled sabadilla seeds from settling in the extraction/washing vessel (e.g., flask).

During the extraction, the sabadilla extract and extract solvent should be agitated. This can be done by any method known by those of skill in the art. The process was most efficient if the stirring was brisk enough to prevent the sediment from the sabadilla extract from settling in the extraction/washing vessel (e.g., flask).

In a preferred embodiment, the seed and plant part solvent is selected from the group consisting of methanol, ethanol, glycol ether, ethyl lactate, and propanol. In a more preferred embodiment, the seed or plant part solvent is methanol.

Methanol can be used at temperatures from about 0 to about 60 degrees Celsius. Applicant found that methanol at lower temperatures required additional extraction time and that temperatures above about 55 to about 60 degrees Celsius resulted in methanol loss and boiling. Applicant found that the optimal temperature for methanol extraction was from about 50 to about 55 degrees Celsius.

In an embodiment, the methanol is removed from the sabadilla extract and solvent solution by evaporation, including distillation.

In another embodiment, the present invention is directed to methods for controlling pests comprising applying the concentrated sabadilla seed extract produced by the methods of the present invention to pests or the pests' environment.

In another embodiment, the pests controlled are selected from the group consisting of members of the class Insecta (insects), Arachnida subclass Acari (mites), and shell-less terrestrial gastropod mollusks (slugs).

In an embodiment, the insects controlled are selected from the group consisting of aphids (Hemiptera), whiteflies (Hemiptera), thrips (Thysanoptera), leafhoppers (Hemiptera), bed bugs (Hemiptera), psyllids (Hemiptera), scale insects (Hemiptera), mealybugs (Hemiptera), psocids (Psocoptera), lice (Phthiraptera), fleas (Siphonaptera), caterpillars (Lepidoptera), and early immature stages of beetles (Coleoptera), true bugs (Hemiptera), cockroaches (Blattodea), flies (Diptera) and wasps (Hymenoptera). In a preferred embodiment, the insects controlled are selected from the group consisting of aphids (Hemiptera), whiteflies (Hemiptera), thrips (Thysanoptera), leafhoppers (Hemiptera), bed bugs (Hemiptera), psyllids (Hemiptera), scale insects (Hemiptera), mealybugs (Hemiptera), psocids (Psocoptera), lice (Phthiraptera), and fleas (Siphonaptera). In a more preferred embodiment, the insects controlled are selected from the group consisting of bed bugs (*Cimex lectularius*), western flower thrips (*Frankliniella occidentalis*), green peach aphids (*Myzus persicae*), and greenhouse whitefly (*Trialeurodes vaporariorum*).

In a preferred embodiment, the mites controlled are two-spotted spider mites (*Tetranychus urticae*).

The sabadilla extract is a contact pesticide which means that the extract should be applied directly to the pests or their environment for the most effective control. The extract, or a formulation containing the extract, can be mixed with water and applied with a pressurized system, such as aerosol generators or in a form of ground application, e.g., low pressure boom sprayers, high pressure sprayers, air blast sprayers, low volume air sprayers (mist blowers), hand-operated sprayers and pump sprays. The extract should be applied as a fine spray until the surface is uniformly wet with minimal runoff. In another embodiment, the extract can be formulated, for example, as granules, and applied by broadcast.

In a further embodiment, the present invention is directed to a concentrated insecticidal sabadilla extract product produced by the process comprising the steps of milling sabadilla seeds, washing the milled sabadilla seeds with at least one seed and plant part solvent selected from the group consisting of methanol, ethanol, glycol ether, ethyl lactate, propanol, butyl lactate, gamma-butyrolactone, and 1-butanol under agitation to produce a sabadilla extract seed and plant part solvent solution, removing the solution from the washed milled seeds, and removing the seed and plant part solvent from the solution to produce the pesticidal sabadilla extract. In a preferred embodiment, the sabadilla seeds can be derived from the *S. officinale.*

As used herein, "concentrated sabadilla extract" refers to an extract of sabadilla seeds or other plant parts which is substantially free of cellulose, hemicellulose, lignin, and pectin.

The concentrated sabadilla extract of the present invention is distinct from sabadilla seeds in their natural state because the extract has been isolated from the seed and concentrated. The sabadilla extract of the present invention is not present in nature in this form.

As used herein, "controlling pests" refers to decreasing the negative impact of pests on plants or animals to a level that is desirable to the grower or animal.

As used herein, "roller mill" refers to equipment used to decrease the shape of a material by pressing the material with at least one cylindrical roller against another roller or firm surface. A roller mill is one way of producing a flaked seed.

As used herein, "pests' environment" refers to any area that the pest is present during any life stage. One environment likely to be treated by the methods of the present invention includes the plants that the pests are living on and the surrounding soil. The pests' environment may include soil, plants, harvested plants, gardens, fields, greenhouses, or other buildings, and various indoor surfaces and structures, such as furniture including beds, and furnishings including books, clothing, etc.

As used herein, all numerical values relating to amounts, weight percentages and the like are defined as "about" or "approximately" each particular value, namely, plus or minus 10% (±10%). For example, the phrase "at least 5% by weight" is to be understood as "at least 4.5% to 5.5% by weight." Therefore, amounts within 10% of the claimed values are encompassed by the scope of the claims.

The articles "a," "an" and "the" are intended to include the plural as well as the singular, unless the context clearly indicates otherwise. For example, the methods of the present invention are directed to controlling "pests" but this can include control of a single pest (such as a single insect).

The following examples are intended to illustrate the present invention and to teach one of ordinary skill in the art how to use the extracts of the invention. They are not intended to be limiting in any way.

EXAMPLES

Example 1

Sabadilla seeds were flake milled according to the manufacturer's instructions. Two hundred grams of milled seed were added to a three liter flask with methanol and stirred with a three blade stirrer controlled by an overhead motor. A stirring speed was maintained which prevented any seed fragments from settling in the flask. The system was sealed to limit evaporation loss.

The methanol was decanted off and additional methanol was added to the flask. This step was repeated three additional times.

The sabadilla extract containing methanol solution was then placed in a new flask. Distillation was used to remove the methanol from the sabadilla extract containing methanol solution. Standard IKA rotary evaporators were used for the distillation. The flask containing the sabadilla extract containing methanol solution was loaded into the evaporator and into a heated water bath. The flask was heated to between 50 to 55 degrees Celsius in order to maximize efficient removal of the methanol without allowing it to boil over into the condenser. The evaporated methanol was thoroughly condensed in an adjoining flask leaving the solute/extract.

Accordingly, a concentrated sabadilla extract was prepared.

We claim:

1. A method for producing a concentrated pesticidal sabadilla extract consisting essentially of: milling sabadilla seeds with a roller mill; washing the milled sabadilla seeds with at least one solvent selected from the group consisting of glycol ether, ethyl lactate, propanol, butyl lactate, gamma-butyrolactone, and 1-butanol under agitation to produce a sabadilla extract containing seed solution; removing the sabadilla extract containing seed solution from the washed milled seeds by counter current extraction; and removing the seed from the solution to procure the concentrated sabadilla extract.

* * * * *